United States Patent [19]
Wolownik

[11] 3,970,710
[45] July 20, 1976

[54] PROCESS FOR MAKING TRIFLUOROETHANOL

[75] Inventor: Stephen Wolownik, Waukegan, Ill.

[73] Assignee: Abbott Laboratories, North Chicago, Ill.

[22] Filed: Apr. 9, 1975

[21] Appl. No.: 566,553

[52] U.S. Cl. .................................... 260/633
[51] Int. Cl.² .......................... C07C 31/34
[58] Field of Search .............. 260/633, 601 H

[56] References Cited
UNITED STATES PATENTS

| | | | |
|---|---|---|---|
| 2,824,897 | 2/1958 | Wajciak et al. | 260/633 |
| 2,982,789 | 5/1961 | Smith et al. | 260/633 |
| 3,468,964 | 4/1969 | Swamer | 260/633 |

*Primary Examiner*—Howard T. Mars
*Attorney, Agent, or Firm*—Paul D. Burgauer; Robert L. Niblack

[57] ABSTRACT

A process for making trifluoroethanol by hydrogenating trifluoroacetyl chloride at elevated temperature over a palladium catalyst.

4 Claims, No Drawings

PROCESS FOR MAKING TRIFLUOROETHANOL

DETAILED DESCRIPTION OF THE INVENTION

One of the newer inhalation anesthetics, isoflurane, recently has found good acceptance in the medical field. The compound involved is the 2,2,2-trifluoro-1-chloroethyl difluoromethyl ether described in U.S. Pat. No. 3,535,388. One of the practical processes for making this compound is described in U.S. Pat. No. 3,637,477; it shows that the best suited approach consists of using 2,2,2-trifluoroethanol (hereinafter referred to as 3FE) as the starting material for making isoflurane. The present invention is concerned with the manufacture of 3FE.

In the past, a number of publications have shown the manufacture of 3FE. In most instances, it is made by reducing or hydrogenating an alkyl ester of trifluoroacetic acid. Other references used, as the starting material for 3FE, the compound trifluoroacetyl chloride which, however, has been reduced successfully only by using a lithium aluminum hydride catalyst. This catalyst is very costly and not easy to handle and, in addition thereto, it cannot be regenerated. Manufacture of 3FE from trifluoroacetyl chloride would otherwise be more convenient than from the corresponding methyl ester or the like because the latter has to be made by some esterification procedure, usually involving trifluoroacetyl chloride as the starting point for making said ester.

It is therefore the primary object of the present invention to make 3FE from trifluoroacetyl chloride. It is another object of this invention to make 3FE from trifluoroacetyl chloride using an inexpensive catalyst that can be regenerated for reuse.

These and other objects are accomplished by the process consisting essentially in heating a mixture of trifluoroacetyl chloride and hydrogen in the presence of palladium supported by alumina to a temperature of 100° – 300°C. The reaction is almost instantaneous and therefore well suited for a continuous operation. A preferred temperature range is between 130° and 200°C. but where continuous operation is desired, it may be preferred to keep the reaction chamber at a constant temperature of between 140° and 185° C. while introducing a continuous feed of hydrogen and trifluoroacetyl chloride. The process of this invention carried out in this fashion is very efficient and produces a high yield of the desired product.

In a general embodiment of this reaction, trifluoroacetyl chloride and at least two molar equivalents of hydrogen are fed continuously into an appropriately heated reaction chamber containing palladium on alumina as the catalyst. The ensuing reaction products are passed through a condenser cooled with acetone/dry ice to collect the condensable products. Operating in this fashion produces yields of 75 – 95% of the desired product.

Temperatures suitable for operating the above continuous process are between room temperature and 300°C. although the higher end of this range is not necessary as will be demonstrated in the examples below. The pressure should be between 1 – 10 atmospheres; higher hydrogen pressures add little to the reaction speed. When operating in a continuous fashion, a gas velocity of between 50 – 2,000 ml. of the gas mixture fed per hour per milliliter of catalyst is preferred. Of course, most efficient use of the starting gases is obtained by feeding them to the reaction chamber in their equimolar ratio.

In order to illustrate the process of the present invention, reference is made to the following examples which, however, are not intended to limit the invention in any form.

EXAMPLE I

A vertically mounted stainless steel tube with an internal diameter of 1.8 cm. and a length of 80 cm. is loaded with 50 ml. of 0.5% palladium-on-alumina in the center portion of the tube. To hold the catalyst in place and to minimize the open space above it, the tube is loaded with ceramic saddles. The reaction tube is equipped with electrical heaters and external air cooling. The reactor is preheated to 160° C. and a gas feed mixture of hydrogen and trifluoroacetyl chloride is fed into the top of the reaction tube. The catalyst containing section of the tube is maintained at 150° – 160°C. by means of air cooling as the reaction is exothermic. The exit stream from the bottom of the reactor is passed through an acetone-dry ice trap. Hydrogen is fed into the reactor at a space velocity of 0.45 moles per hour and the trifluoroacetyl chloride is introduced at a rate of 0.183 moles per hour. Over a period of 90 minutes, 28 g. of product is collected in the dry ice trap. The product assays 86.6% of 3FE by gas chromatography which amounts to 3FE per-pass yield of 88.2%.

EXAMPLES 2 – 8

In accordance with the procedure in Example 1, other temperatures and feed rate ratios are used. In all these examples, 50 ml. of catalyst is used in the reactor except in Examples 7 and —8 where 100 ml. of catalyst is used. The results of these runs are shown in the table below.

TABLE

| Ex. No. | Average Catalyst Hot Spot Temperature (°C.) | Feed Rate (gm. moles per hour) Hydrogen | CF$_3$COCl | Product Recovered per Hour (gms) | % 3FE in Product (g.c.) | Per Pass Yield of 3FE |
|---|---|---|---|---|---|---|
| 2 | 133°C. | 0.45 | 0.189 | 17.6 | 83.8% | 77.9% |
| 3 | 167°C | 0.45 | 0.183 | 18.3 | 89.2 | 89.1 |
| 4 | 183°C | 0.45 | 0.180 | 18.6 | 91.9 | 94.9 |
| 5 | 200°C | 0.45 | 0.181 | 18.3 | 90.9 | 91.9 |
| 6 | 230°C | 0.45 | 0.186 | 18.1 | 80.0 | 77.7 |
| 7 | 230°C | 0.94 | 0.332 | 29.6 | 79.3 | 79.4 |
| 8 | 256°C | 0.94 | 0.281 | 29.5 | 79.6 | 83.6 |

As will be seen from the above examples, the present process produces excellent returns of 3FE over short periods with excellent yields based on the trifluoroacetyl chloride used in the reaction.

While a wide range of temperatures can be used for the process of this invention, it should be noted that temperatures of 130° C. or above produce better conversion rates than lower temperatures. The reaction takes place at any pressure and there is no need to pressurize the reaction tube as long as the reactants are present in the molecular ratio in which they take part in the reaction. However, where a batch operation is desired, the trifluoroacetyl chloride may be placed in the reactor with the catalyst and hydrogen gas is then best introduced at a pressure sufficient to overcome the vapor pressure of the trifluoroacetyl chloride gas in the reaction vessel.

It should be kept in mind that, in a continuous reaction, the mixture of the gases requires a contact time with the catalyst of only a few seconds, i.e. 5 – 10 seconds. At elevated temperatures, the contact time required between the gas mixture and the catalyst is only a fraction of the above since the reaction is essentially instantaneous. Thus, the reaction can be carried out by continuously supplying the reactants into the reaction vessel at elevated pressure or by applying a vacuum to the outlet of said vessel.

A particular advantage of the present invention is the low cost of the catalyst as it can be regenerated by simple heating in the presence of oxygen to a temperature of about 200° C. Even without regeneration, a catalyst bed remains active for periods of 24 hours and more.

It is surprising and unexpected that of all the possible known hydrogenation catalysts, only palladium can be used for the instant process. When platinum or ruthenium are used, for instance, the yield of the above process is found to be only a minor fraction of the yield obtained with palladium.

The palladium used in the present invention can be supported by alumina or other inert supports, i.e. silica gel, bentonite or similar materials that withstand the temperature used in this process.

In view of the fact that the current process takes place between gases, the reaction is preferably carried out on a continuous basis, i.e. by passing the mixture of trifluoroacetyl chloride and hydrogen in an equimolar amount over the catalyst bed placed in a properly heated chamber. Contact times of ten seconds or less are suitable, and if desired, the gas mixture is preheated before entering the catalyst chamber. The instantaneously formed 3FE condenses at temperatures below −27° C. at atmospheric pressure, thus requiring a dry ice condenser. However, the desired product can be liquified under higher pressure above said temperature.

What is claimed is:

1. The process of preparing 2,2,2-trifluoroethanol comprising the single step of heating a mixture of trifluoroacetyl chloride and hydrogen in the presence of palladium supported by alumina at a temperature of 100°–300° C. and condensing the formed 2,2,2 - trifluoroethanol at a temperature below its boiling point.

2. The process of claim 1 wherein said temperature is between 140° and 185°C.

3. The process of claim 1 wherein said trifluoroacetyl chloride and said hydrogen are present in equimolar amounts.

4. The process of claim 1 wherein said trifluoroacetyl chloride and said hydrogen are passed as a gaseous mixture over said palladium at a temperature of 140°–185° C.

* * * * *